United States Patent [19]

Aoyagi et al.

[11] Patent Number: 4,933,103
[45] Date of Patent: Jun. 12, 1990

[54] BLEACHING COMPOSITION

[75] Inventors: Muneo Aoyagi; Kazuhiro Takanashi, both of Utsunomiya; Hiroyuki Araki, Ichikai; Moriyasu Murata, Chiba; Kohshiro Sotoya; Nobuyuki Ogura, both of Wakayama; Masaaki Yamamura, Utsunomiya, all of Japan

[73] Assignee: Kao Corporation, Tokyo, Japan

[21] Appl. No.: 166,880

[22] Filed: Mar. 11, 1988

[30] Foreign Application Priority Data

Mar. 23, 1987 [JP] Japan .................. 62-68636
Mar. 23, 1987 [JP] Japan .................. 62-68637
Jan. 25, 1988 [JP] Japan .................. 63-14243

[51] Int. Cl.$^5$ .................. A62D 3/00; C01B 15/00; C09K 3/00
[52] U.S. Cl. .................. 252/186.38; 252/186.41; 252/186.42; 252/186.43
[58] Field of Search .................. 252/186.41, 186.42, 252/186.43, 186.23, 186.22, 186.39, 186.38

[56] References Cited

U.S. PATENT DOCUMENTS 3,272,750  9/1966  Chase .................. 252/186.38
4,124,356 11/1978 Blumbergs et al. ........ 252/186.23 X
4,397,757  8/1983 Bright et al. .................. 252/186.41
4,412,934 11/1983 Chung et al. .................. 252/186.38
4,525,292  6/1985 Cushman et al. .............. 252/186.38
4,634,551  1/1987 Burns et al. .................... 252/186.28
4,681,592  7/1987 Hardy et al. .................... 252/186.28
4,686,061  8/1987 Nollet et al. .................... 252/186.38
4,751,015  6/1988 Humphreys et al. .......... 252/186.38
4,772,290  9/1988 Mitchell et al. ................ 252/186.23

Primary Examiner—Matthew A. Thexton
Assistant Examiner—Joseph D. Anthony
Attorney, Agent, or Firm—Flynn, Thiel, Boutell & Tanis

[57] ABSTRACT

A bleaching composition comprises a peroxide and an amphoteric organic per acid precursor. In particular the amphoteric organic per acid precursor is a quaternary ammonium salt has the following formula in which Z is sulfonate or carboxylate and is a new compound.

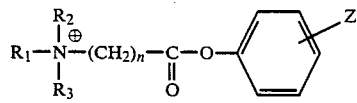

14 Claims, No Drawings

BLEACHING COMPOSITION

The invention relates to a bleaching composition and a novel amphoteric compound to serve as an activator for the composition.

STATEMENT OF THE PRIOR ARTS

Since chlorine-containing bleaching agents have the defects that the textiles to which they are applicable are limited, that they cannot be used for bleaching colored or figured cloths and that they have a peculiar smell, the use of oxygen-containing bleaching agents free of these defects has generally spread recently.

Among the oxygen-containing bleaching agents, sodium percarbonate and sodium perborate are particularly useful in virtue of their bleaching capacity and stability.

The oxygen-containing bleaching agents are used in combination with various bleaching activators, since their bleaching power is weaker than that of the chlorine-containing ones. Investigations have been made on various bleaching activators including, for examples, nitriles such as acetonitrile, malononitrile, phthalonitrile and benzoyliminodiacetonitrile; O-acetylated compounds such as glucose pentaacetate, octaacetylsucrose, triacetin, sorbitol hexaacetate, acetoxybenzenesulfonates, triacetylcyanuric acid and methyl chloroformate; N-acylated compounds such as N,N,N',N'-tetraacetylethylenediamine and tetraacetylglycolyluril, N-benzoylimidazole, di-N-acetyldimethylglyoxime, 1-phenyl-3-acetylhydantoin, N,N-diacetylaniline, N-acetyldiglycolimide and diacetylmethylenediformamide; acid anhydrides such as phthalic, succinic, benzoic, glutaric, alkylsulfuric and carboxylic/organic sulfonic acid anhydrides; sulfonyl oximes such as di(methanesulfonyl)-dimethylglyoxime; acylated phosphoric acid salts such as diethylbenzoylphosphoric acid salts; phenyl sulfonate esters; organic phosphoric azides such as diphenylphosphinic azides; disulfones such as diphenyl disulfone; and other compounds such as N-sulfonylimidazole, cyanamide, halogenated triazines and N,N-dimethyl-N-octyl-N-10-carbophenoxydodecylammonium chloride. However, no sufficient bleaching power could be obtained even when such an activator was used in combination with the oxygen-containing bleaching agent.

SUMMARY OF THE INVENTION

After intensive investigations made for the purpose of developing an oxygen-containing bleaching agent having a higher bleaching power, the inventors have found that the object can be attained by using a combination of a peroxide and an amphoteric organic per acid precursor. The present invention has been completed on the basis of this finding.

A bleaching composition of the invention comprises a peroxide and an amphoteric organic per acid precursor, preferably at a molar ratio of 99.9/0.1 to 20/80.

The organic per acid precursor is preferred to be an amphoteric compound having the formula (I):

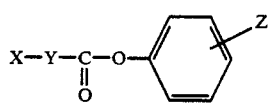

wherein: X represents a group of the formula:

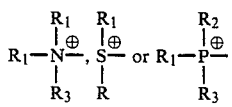

in which $R_1$ and $R_2$ each represents a substituted or unsubstituted, straight-chain or branched alkyl or alkenyl group having 1 to 30 carbon atoms, an alkaryl group (in which the alkyl group has 1 to 24 carbon atoms) or the two R groups may form a heterocyclic ring having 4 to 6 carbon atoms, together with N, S or P, $R_3$ represents a substituted or unsubstituted, straight-chain or branched alkyl or alkenyl group having 1 to 30 carbon atoms, an alkaryl group (in which the alkyl group has 1 to 16 carbon atoms) or a heterocyclic ring having 4 to 6 carbon atoms together with the two R groups bonded to N, S or P or $-(C_2H_4O)_xH$ (in which x is a number of 1 to 20), Y represents a straight-chain or branched alkylene group having 1 to 20 carbon atoms, and Z represents an $SO_3^-$ or $CO_2^-$ group.

It is more preferable that in the formula (I) X is $-N^+R_1R_2R_3$, $R_1$ is an alkyl having 1 to 22 carbon atoms or a hydroxyalkyl having 1 to 22 carbon atoms and $R_2$ and $R_3$ each are an alkyl having 1 to 3 carbon atoms, Y is an alkylene having 1 to 5 carbon atoms and Z is sulfonate or carboxylate.

The composition of the invention may further contain a conventional detergent component.

The invention provides an amphoteric compound having the formula (V):

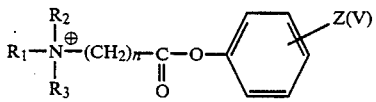

in which $R_1$ is an alkyl group having 1 to 22 carbon atoms, $R_2$ and $R_3$ each are a lower alkyl, n is an integer of 1 to 5, Z is $-COO^-$, $-COOM$, $-SO_3^-$ or $-SO_3M$ and M is a cation.

The compound having the formula (V) in which $R_1$ is an alkyl having 1 to 16 carbon atoms and $R_2$ and $R_3$ each are an alkyl having 1 to 3 carbon atoms preferably provides the bleaching effect. In particular the compound having methyl for $R_1$ is useful from the practical point of view. In addition, the compound in which $R_1$ is an alkyl having 8 to 16 carbon atoms does not only provide the bleaching effect, but also the surface activity.

The compound having the formula (I) in which Z is $-SO_3^-$ can be obtained, for example, by the following process:

a tertiary amine is reacted with a halocarboxylic acid in a solvent such as an alcohol or acetone at room temperature or under reflux of the solvent to obtain a quarternary amine (II):

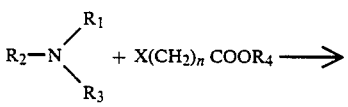

-continued

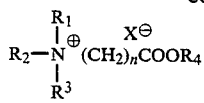

wherein $R_1$, $R_2$, $R_3$ and $R_4$ each represents an alkyl group, n represents an integer of 1 to 5 and X represents a halogen atom.

Then, the compound (II) is hydrolyzed in the presence of an alkaline catalyst such as KOH or NaOH in a solvent mixture such as a mixture of water with an alcohol to obtain an amphoteric compound (III):

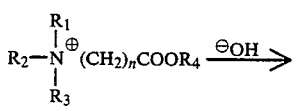 (III)

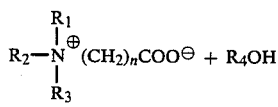

The compound (III) is reacted with thionyl chloride in dichloromethane or ethanol-free chloroform, i.e., in a solvent free from any compound reactive with an acyl chloride, such as water or an alcohol, to obtain an acyl chloride (IV):

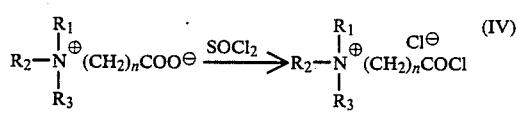 (IV)

The obtained chloride (IV) is reacted with disodium p-phenolsulfonate in a solvent in which the compound (IV) is soluble or homogeneously dispersible, such as dimethoxyethane (DME), under reflux of the solvent to obtain an intended amphoteric compound (I):

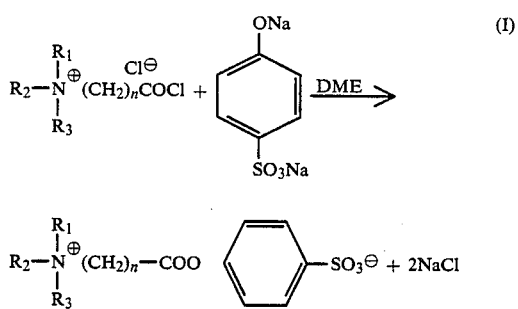 (I)

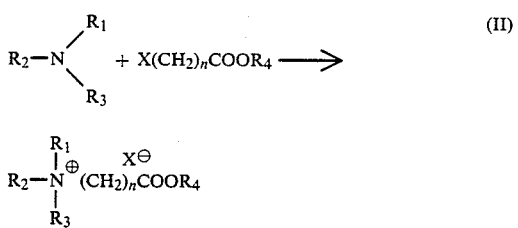

The compound having the formula (I) in which Z is $-CO_2^-$ can be obtained, for example, by the following process:

wherein $R_1$, $R_2$, $R_3$ and $R_4$ stand for each an alkyl group, n is an integer of from 1 to 5 and X stands for a halogen atom.

Then, the compound (II) is hydrolyzed with an alkali catalyst such as KOH or NaOH in a mixed solvent such as water/alcohol to obtain an amphoteric compound represented by the formula (III), as indicated below:

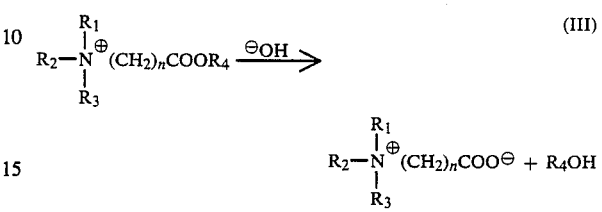 (III)

The compound (III) is reacted with thionyl chloride in the presence of a solvent not containing a substance capable of reacting with an acid chloride, such as water or an alcohol, for example, in dichloromethane or chloroform subjected to an ethanol-removing treatment, to obtain an acid chloride of the formula (IV), as indicated below:

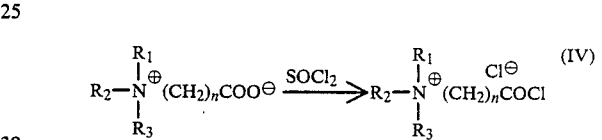 (IV)

Then, the acid chloride (IV) is reacted with p-hydroxybenzoic acid (typical instance) in tetrahydrofuran (THF) as the solvent to obtain the intended amphoteric compound (I).

The amphoteric organic per acid precursor remarkably improves the bleaching power of the peroxide.

The peroxide in the present invention is preferably hydrogen peroxide or a peroxide capable of generating hydrogen peroxide in its aqueous solution.

The peroxides capable of generating hydrogen peroxide in an aqueous solution thereof include organic and inorganic hydrogen peroxide adducts such as sodium carbonate/hydrogen peroxide adduct, sodium tripolyphosphate/hydrogen peroxide adduct, sodium pyrophosphate/hydrogen peroxide adduct, urea/hydrogen peroxide adduct and $4Na_2SO_4 \cdot 2H_2O_2 \cdot NaCl$. They further include inorganic peroxides such as sodium perborate monohydrate, sodium perborate tetrahydrate, sodium peroxide and calcium peroxide. Among them, sodium carbonate/hydrogen peroxide adduct, sodium perborate monohydrate and sodium perborate tetrahydrate are particularly preferred.

The molar ratio of the peroxide to the organic per acid precursor used in the present invention is 99.9/0.1 to 20/80.

The bleaching composition of the present invention may contain known additives usually contained in bleaching compositions in addition to the above-mentioned indispensable components. For example, the composition may contain a builder such as a water-soluble inorganic builder, e.g., sulfate, carbonate, bicarbonate, silicate or phosphate or an organic builder, e.g., ethylenediaminetetraacetate, tartrate or citrate. Stabilizers for the peroxide or hydrogen peroxide adduct usable in the present invention include known magnesium salts such as magnesium sulfate, magnesium silicate, magnesium chloride, magnesium fluorosilicate, magnesium oxide and magnesium hydroxide, and silicates such as sodium silicate. If necessary, the bleaching composition may further contain an antiredeposition agent such as carboxymethylcellulose, polyvinylpyrrolidone or polyethylene glycol, as well as surfactant, enzyme, fluorescent brightener, dye, pigment, flavor, etc.

The bleaching detergent composition of the invention may comprises the following in addition to the above shown bleaching agents.

[1] SURFACTANTS (1) Straight-chain or branched alkylbenzenesulfonate salts having an alkyl group of 10–16 carbon atoms on the average.

(2) Alkyl or alkenyl ether sulfate salts having a straight-chain or branched alkyl or alkenyl group of 10–20 carbon atoms on the average, 0.5–8 mol on the average of ethylene oxide, propylene oxide or butylene oxide in the molecule and an addition ratio of ethylene oxide/propylene oxide of 0.1/9.9–9.9/0.1 or ethylene oxide/butylene oxide of 0.1/9.9–9.9/0.1

(3) Alkyl or alkenyl sulfate salts having an alkyl or alkenyl group of 10–20 carbon atoms on the average.

(4) Olefinsulfonate salts having 10–20 carbon atoms on the average in the molecule.

(5) Alkanesulfonate salts having 10–20 carbon atoms on the average in the molecule.

(6) Saturated or unsaturated fatty acid salts having 10–24 carbon atoms on the average in the molecule.

(7) Alkyl or alkenyl ether carboxylate salts having an alkyl or alkenyl group of 10–20 carbon atoms on the average, 0.5–8 mol on the average of ethylene oxide, propylene oxide or butylene oxide in the molecule and an addition ratio of ethylene oxide/propylene oxide of 0.1/9.9–9.9/0.1 or ethylene oxide/butylene oxide of 0.1/9.9 to 9.9/0.1.

(8) α-Sulfo fatty acid salts or esters of the general formula:

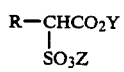

wherein Y represents an alkyl group having 1–3 carbon atoms or a counter-ion, Z represents a counter-ion and R represents an alkyl or alkenyl group having 10–20 carbon atoms.

As the counter-ions of anionic surfactants, there may be mentioned, for example, ions of alkali metals such as sodium and potassium, alkaline earth metals such as calcium and magnesium, ammonium, alkanolamines containing 1–3 alkanol groups having 2 or 3 carbon atoms such as monoethanolamine, diethanolamine, triethanolamine and triisopropanolamine.

(9) Amino acid-type surfactants of the general formulae:

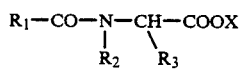 No. 1 wherein $R_1$ represents an alkyl or alkenyl group having 8–24 carbon atoms, $R_2$ represents hydrogen or an alkyl group having 1–2 carbon atoms, $R_3$ represents an amino acid residue and X represents an alkali metal or alkaline earth metal ion.

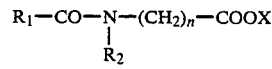 No. 2 wherein $R_1$, $R_2$ and X have the same meanings as above and n represents an integer of 1–5.

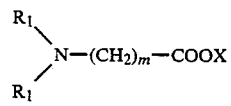 No. 3 wherein $R_1$ has the same meaning as above and m represents an integer of 1–8.

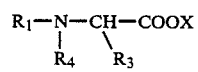 No. 4 wherein $R_1$, $R_3$ and X have the same meaning as above and $R_4$ represents hydrogen, or an alkyl or hydroxyalkyl group having 1–2 carbon atoms.

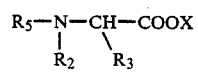 No. 5 wherein $R_2$, $R_3$ and X have the same meaning as above and $R_5$ represents a β-hydroxyalkyl or β-hydroxyalkenyl group having 6–28 carbon atoms.

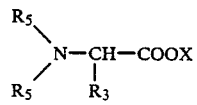 No. 6 wherein $R_3$, $R_5$ and X have the same meaning as above.

(10) Phosphate ester surfactants:

No. 1 Acid alkyl (or alkenyl) phosphates:

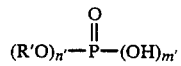

wherein R' represents an alkyl or alkenyl group having 8–24 carbon atoms, $n'+m'$ represents 3 and $n'$ represents a number of 1–2.

No. 2 Alkyl (or alkenyl) phosphates:

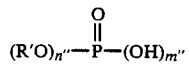

wherein R' has the same meaning as above, $n''+m''$ represents a number of 3 and $n''$ represents a number of 1–3.

No. 3 Alkyl (or alkenyl) phosphate salts:

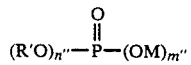

wherein R', $n''$ and $m''$ have the same meaning as above and M represents Na, K or Ca.

(11) Sulfonic acid-type amphoteric surfactants of the general formulae:

$$\underset{\underset{R_{13}}{|}}{R_{11}CONH-R_{12}-\overset{\overset{R_{13}}{|}}{N^{\oplus}}-R_{14}-SO_3^{\ominus}} \quad \text{No. 1}$$

wherein $R_{11}$ represents an alkyl or alkenyl group having 8–24 carbon atoms, $R_{12}$ represents an alkylene group having 1–4 carbon atoms, $R_{13}$ represents an alkyl group having 1–5 carbon atoms, $R_{14}$ represents an alkylene or hydroxyalkylene group having 1–4 carbon atoms.

$$\underset{\underset{R_{16}}{|}}{R_{11}-\overset{\overset{R_{15}}{|}}{N^{\oplus}}-R_{14}-SO_3^{\ominus}} \quad \text{No. 2}$$

wherein $R_{11}$ and $R_{14}$ have the same meaning as above and $R_{15}$ and $R_{16}$ each represent an alkyl or alkenyl group having 8–24 or 1–5 carbon atoms.

$$\underset{\underset{(C_2H_4O)_{n1}H}{|}}{R_{11}-\overset{\overset{(C_2H_4O)_{n1}H}{|}}{N^{\oplus}}-R_{14}-SO_3^{\ominus}} \quad \text{No. 3}$$

wherein $R_{11}$ and $R_{14}$ have the same meaning as above and n1 represents an integer of 1–20.

(12) Betaine-type, amphoteric surfactants of the general formulae:

$$\underset{\underset{R_{22}}{|}}{R_{21}-\overset{\overset{R_{22}}{|}}{N^{\oplus}}-R_{23}-COO^{\ominus}} \quad \text{No. 1}$$

wherein $R_{21}$ represents an alkyl, alkenyl, β-hydroxyalkyl or β-hydroxyalkenyl group having 8–24 carbon atoms, $R_{22}$ represents an alkyl group having 1–4 carbon atoms and $R_{23}$ represents an alkylene or hydroxyalkylene group having 1–6 carbon atoms.

$$\underset{\underset{(C_2H_4O)_{n2}H}{|}}{R_{21}-\overset{\overset{(C_2H_4O)_{n2}H}{|}}{N^{\oplus}}-R_{23}-COO^{\ominus}} \quad \text{No. 2}$$

wherein $R_{21}$ and $R_{23}$ have the same meaning as above and n2 represents an integer of 1–20.

$$\underset{\underset{R_{24}}{|}}{R_{21}-\overset{\overset{R_{24}}{|}}{N^{\oplus}}-R_{23}-COO^{\ominus}} \quad \text{No.3}$$

wherein $R_{21}$ and $R_{23}$ have the same meaning as above and $R_{24}$ represents a carboxyalkyl or hydroxyalkyl group having 2–5 carbon atoms.

(13) Polyoxyethylene alkyl or alkenyl ethers having an alkyl or alkenyl group of 10–20 carbon atoms on the average and 1–30 mol of ethylene oxide added.

(14) Polyoxyethylene alkylphenyl ethers having an alkyl group of 6–12 carbon atoms on the average and 1–25 mol of ethylene oxide added.

(15) Polyoxypropylene alkyl or alkenyl ethers having an alkyl or alkenyl group of 10–20 carbon atoms on the average and 1–20 mol of propylene oxide added.

(16) Polyoxybutylene alkyl or alkenyl ethers having an alkyl or alkenyl group of 10–20 carbon atoms on the average and 1–20 mol of butylene oxide added.

(17) Nonionic surfactants having an alkyl or alkenyl group of 10–20 carbon atoms on the average and 1–30 mol in total of ethylene oxide and propylene oxide added or ethylene oxide and butylene oxide added (ratio of ethylene oxide to propylene oxide or butylene oxide being 0.1/9.9 to 9.9/0.1).

(18) Higher fatty acids alkanolamides or alkylene oxide adducts thereof of the general formula:

$$R'_{11}CON\begin{matrix}(\overset{R'_{12}}{\overset{|}{C}HCH_2O})_{n3}H \\ \\ (\underset{R'_{12}}{\underset{|}{C}HCH_2O})_{m3}H\end{matrix}$$

wherein $R'_{11}$ represents an alkyl or alkenyl group having 10–20 carbon atoms, $R'_{12}$ represents H or $CH_3$, n3 represents an integer of 1–3 and m3 represents an integer of 0–3.

(19) Sucrose/fatty acid esters comprising fatty acids having 10–20 carbon atoms on the average and sucrose.

(20) Fatty acid/glycerol monoesters comprising fatty acids having 10–20 carbon atoms on the average and glycerol.

(21) Alkylamine oxides of the general formula:

$$\underset{\underset{R'_{15}}{|}}{R'_{13}-\overset{\overset{R'_{14}}{|}}{N}\longrightarrow O}$$

wherein $R'_{13}$ represents an alkyl or alkenyl group having 10–20 carbon atoms and $R'_{14}$ and $R'_{15}$ each represent an alkyl group having 1–3 carbon atoms.

(22) Cationic surfactants of the general formulae:

$$[R'_1-\overset{\overset{R'_2}{|}}{\underset{\underset{R'_3}{|}}{N^{\oplus}}}-R'_4]X'^{\ominus} \quad \text{No. 1}$$

wherein at least one of $R'_1$, $R'_2$, $R'_3$ and $R'_4$ represents an alkyl or alkenyl group having 8–24 carbon atoms and the remainder represents an alkyl group having 1–5 carbon atoms and $X'$ represents a halogen.

$$[R'_1-\overset{\overset{R'_2}{|}}{\underset{\underset{R'_3}{|}}{N^{\oplus}}}-CH_2C_6H_5]X'^{\ominus} \quad \text{No. 2}$$

wherein $R'_1$, $R'_2$, $R'_3$ and $X'$ have the same meaning as above.

$$[R'_1-\overset{\overset{(R'_5O)_{n4}H}{|}}{\underset{\underset{(R'_5O)_{n4}H}{|}}{N^{\oplus}}}-R'_2]X'^{\ominus} \quad \text{No. 3}$$

wherein $R'_1$, $R'_2$ and $X'$ have the same meaning as above, $R'_5$ represents an alkylene group having 2–3 carbon atoms and n4 represents an integer of 1–20.

The composition probably contains at least one of the above surfactants in an amount of at least 10 wt. %.

As preferred surfactants, there may be mentioned above surfactants (1), (2), (3), (4), (5), (6), (11)-No. 2, (12)-No. 1, (13), (14), (15), (17) and (18).

[2] DIVALENT METAL ION SEQUESTERING AGENTS

The composition may contain 0–50 wt. % of one or more builder components selected from the group consisting of alkali metal salts or alkanolamine salts of the following compounds:

(1) Salts of phosphoric acids such as orthophosphoric acid, pyrophosphoric acid, tripolyphosphoric acid, metaphosphoric acid, hexametaphosphoric acid and phytic acid.

(2) Salts of phosphonic acids such as ethane-1,1-diphosphonic acid, ethane-1,1,2-triphosphonic acid, ethane-1-hydroxy-1,1-diphosphonic acid and its derivatives, ethane-hydroxy-1,1,2-triphosphonic acid, ethane-1,2-dicarboxy-1,2-diphosphonic acid and methanehydroxyphosphonic acid.

(3) Salts of phosphono carboxylic acids such as 2-phosphonobutane-1,2-dicarboxylic acids, 1-phosphonobutane-2,3,4-tricarboxylic acids and α-methylphosphonosuccinic acid.

(4) Salts of amino acids such as aspartic acid, glutamic acid and glycine.

(5) Salts of aminopolyacetic acids such as nitrilotriacetic acid, iminodiacetic acid, ethylenediaminetetraacetic acid, diethylenetriaminepentaacetatic acid, glycol ether diaminetetraacetic acid, hydroxyethyliminodiacetic acid, triethylenetetraminehexaacetic acid and dienkolic acid.

(6) High-molecular electrolytes such as polyacrylic acid, polyaconitic acid, polyitaconic acid, polycitraconic acid, polyfumaric acid, polymaleic acid, polymesaconic acid, poly-α-hydroxyacrylic acid, polyvinylphosphonic acid, sulfonated polymaleic acid, maleic anhydride/diisobutylene copolymer, maleic anhydride/styrene copolymer, maleic anhydride/methyl vinyl ether copolymer, maleic anhydride/ethylene copolymer, maleic anhydride/ethylene cross-linked copolymer, maleic anhydride/vinyl acetate copolymer, maleic anhydride/acrylonitrile copolymer, maleic anhydride/acrylate ester copolymer, maleic anhydride/butadiene copolymer, maleic anhydride/isoprene copolymer, poly-β-keto carboxylic acid derived from maleic anhydride and carbon monoxide, itaconic acid/ethylene copolymer, itaconic acid/aconitic acid copolymer, itaconic acid/maleic acid copolymer, itaconic acid/acrylic acid copolymer, malonic acid/methylene copolymer, mesaconic acid/fumaric acid copolymer, ethylene glycol/ethylene terephthalate copolymer, vinylpyrrolidone/vinyl acetate copolymer, 1-butene-2,3,4-tricarboxylic acid/itaconic acid/acrylic acid copolymer, quaternary ammonium group-containing polyester polyaldehyde carboxylic acids, cis-isomer of epoxysuccinic acid, poly[N,N-bis(carboxymethyl)acrylamide], poly(hydroxy carboxylic acid), starch succinate, starch maleate, starch terephthalate, starch phosphate ester, dicarboxystarch, dicarboxymethylstarch and cellulose succinate esters.

(7) Non-dissociating high-molecular compounds such as polyethylene glycol, polyvinyl alcohol, polyvinylpyrrolidone and cold water-soluble, urethanated polyvinyl alcohol.

(8) Salts of dicarboxylic acids such as oxalic acid, malonic acid, succinic acid, glutaric acid, adipic acid, pimelic acid, suberic acid, azelaic acid and decane-1,10-dicarboxylic acid; salts of diglycolic acid, thiodiglycolic acid, oxalacetic acid, hydroxydisuccinic acid, carboxymethylhydroxysuccinic acid and carboxymethyltartronic acid; salts of hydroxy carboxylic acids such as glycolic acid, malic acid, hydroxypivalic acid, tartaric acid, citric acid, lactic acid, gluconic acid, mucic acid, glucuronic acid and dialdehydostarch oxide; salts of itaconic acid, methylsuccinic acid, 3-methylglutaric acid, 2,2-dimethylmalonic acid, maleic acid, fumaric acid, glutamic acid 1,2,3-propanetricarboxylic acid, aconitic acid, 3-butene-1,2,3-tricarboxylic acid, butane-1,2,3,4-tetracarboxylic acid, ethanetetracarboxylic acid, ethenetetracarboxylic acid, n-alkenylaconitic acid, 1,2,3,4-cyclopentanetetracarboxylic acid, phthalic acid, trimesic acid, hemimellitic acid, pyromellitic acid, benzenehexacarboxylic acid, tetrahydrofuran-1,2,3,4-tetracarboxylic acid and tetrahydrofuran-2,2,5,5-tetracarboxylic acid; salts of sulfonated carboxylic acids such as sulfoitaconic acid, sulfotricarballylic acid, cysteic acid, sulfoacetic acid and sulfosuccinic acid; carboxymethylated sucrose, lactose and raffinose, carboxymethylated pentaerythritol, carboxymethylated gluconic acid, condensates of polyhydric alcohols or saccharides with maleic anhydride or succinic anhydride, condensates of hydroxy carboxylic acids with maleic anhydride or succinic anhydride, and organic acid salts such as CMOS and Builder M.

(9) Aluminosilicates:

No. 1. Crystalline aluminosilicates of the formula:

$$x'(M'_2O \text{ or } M''O)\cdot Al_2O_3\cdot y'(SiO_2)\cdot w'(H_2O)$$

wherein $M'$ represents an alkali metal atom, $M''$ represents an alkaline earth metal atom exchangeable with calcium, and $x+$, $y'$ and $w'$ represent mole numbers of the respective components and generally, they are as follows: $0.7 \leq x' \leq 1.5$, $0.8 \leq y' \leq 6$ and $w'$ being a positive number.

No. 2. Detergent builders having the following general formula are particularly preferred:

$$Na_2O\cdot Al_2O_3\cdot nSiO_2\cdot wH_2O$$

wherein n represents a number of 1.8–3.0 and w represents a number of 1–6.

No. 3. Amorphous aluminosilicates of the formula:

$$x(M_2O)\cdot Al_2O_3\cdot y(SiO_2)\cdot w(H_2O)$$

wherein M represents sodium and/or potassium atom, and x, y and w represent mole numbers of the respective components within the following ranges:

$$0.7 \leq x \leq 1.2$$

$$1.6 \leq y \leq 2.8$$

w: any positive number including O.

No. 4. Amorphous aluminosilicates of the formula:

$$X(M_2O)\cdot Al_2O_3\cdot Y(SiO_2)\cdot Z(P_2O_5)\cdot \omega(H_2O)$$

wherein M represents Na or K and X, Y, Z and ω represent mole numbers of the respective components within the following ranges:

$0.20 \leq X \leq 1.10$ $0.20 \leq Y \leq 4.00$ $0.001 \leq Z \leq 0.80$

ω: any positive number including 0.

Carbohydrolases include alkali cellulases, maltase, saccharase, amylase, pectinase, lysozyme, α-glycosidase and β-glucosidase.

[6] BLUING AGENTS AND FLUORESCENT DYES

Various bluing agents and fluorescent dyes may be incorporated in the composition, if necessary. For example, compounds of the following structures are recommended:

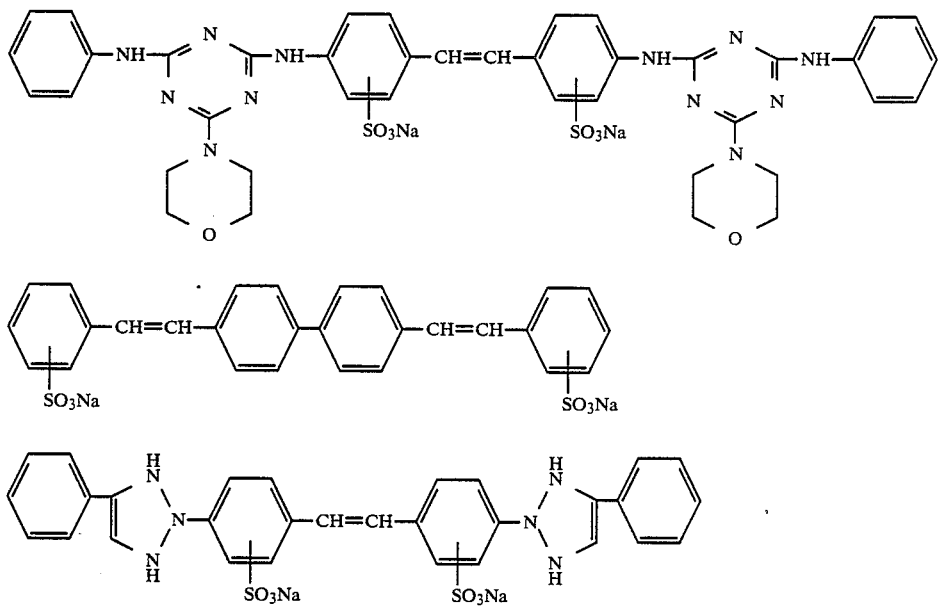

[3] ALKALIS OR INORGANIC ELECTROLYTES

The composition may contain also 1-50 wt. %, preferably 5-30 wt. %, of one or more alkali metal salts selected from the following compounds as the alkali or inorganic electrolyte: silicates, carbonates and sulfates. Further, the composition may contain organic alkalis such as triethanolamine, diethanolamine, monoethanolamine and triisopropanolamine.

[4] ANTIREDEPOSITION AGENTS

The composition may contain 0.1-5% of one or more of the following compounds as antiredeposition agent(s): polyethylene glycol, polyvinyl alcohol, polyvinylpyrrolidone and carboxymethylcellulose.

[5] ENZYMES (enzymes which exhibits the essential enzymatic effects thereof in the derging step)

As the enzymes, the following enzymes may be mentioned (classified with respect to their enzymatic reactivities): Hydrolases, hydrases, oxido-reductases, desmolases, transferases and isomerases. All of these enzymes may be used in the present invention. Particularly preferred enzymes are hydrolases such as proteases, esterases, carbohydrolases and nucleases.

Examples of proteases are pepsin, trypsin, chymotrypsin, collagenase, keratinase, elastase, subtilisin, BPN, papain, bromelin, carboxypeptidases A and B, aminopeptidase and aspergillopeptidases A and B.

Examples of esterases are gastric lipase, pancreatic lipase, vegetable lipases, phospholipases, cholinesterases and phosphotases.

and bluing agents of the general formulae:

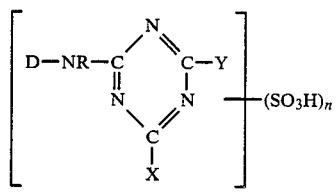

wherein D represents a residue of blue or purple, monoazo, disazo or anthraquinone dye, X and Y each represent hydroxyl group, amino group, an aliphatic amino group which may be substituted with hydroxyl, sulfonic acid, carboxylic acid or alkoxyl group, or an aromatic or alicyclic amino group which may be substituted with a halogen atom or hydroxyl, sulfonic acid, carboxylic acid, lower alkyl or lower alkoxyl group, R represents a hydrogen atom or a lower alkyl group but excluding cases wherein (1) R represents a hydrogen atom and both X and Y represent a hydroxyl group or an alkanolamine at the same time and (2) R represents a hydrogen atom, one of X and Y represents a hydroxyl group and the other represents an alkanolamine group, and n represents an integer of at least 2, and

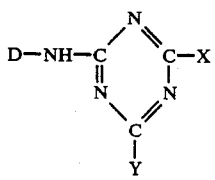

wherein D represents a residue of a blue or purple, azo or anthraquinone dye, and X and Y may be the same or different and represent an alkanolamine residue or a hydroxyl group.

[7] CAKING-PREVENTING AGENTS

The following caking-preventing agents may be incorporated in powdery detergent composition: p-toluenesulfonate salts, xylenesulfonate salts, acetate salts, sulfosuccinate salts, talc, finely pulverized silica, clay, calcium silicates (such as Micro-Cell of Johns-Manvill Co.), calcium carbonate and magnesium oxide.

[8] ANTIOXIDANTS

The antioxidants include, for example, tert-butylhydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1'-bis(4-hydroxyphenyl)cyclohexane.

[9] STABILIZER FOR THE PEROXIDE AND AN ADDUCT TO HYDROGEN PEROXIDE

A stabilizer may be used in the bleaching detergent composition, including a magnesium salt such as magnesium sulfate, magnesium silicate, magnesium chloride, magnesium silicofluoride, magnesium oxide and magnesium hydroxide and a silicate such as sodium silicate.

EXAMPLES

The following examples will further illustrate the present invention, which by no means limit the invention.

Example 1

Preparation of

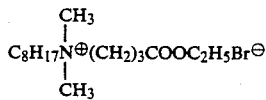

62.8 g of dimethyloctylamine was dissolved in 300 ml of ethanol in a 1-l two-necked flask provided with a condenser tube. 78.0 g of ethyl bromobutyrate was added dropwise to the solution. After the completion of the addition, the temperature was elevated in an oil bath (90° C.) and the reaction was continued until the starting amine became no more detectable under reflux of ethanol under examination according to TLC. Thus, ethanol was distilled off to obtain 140.5 g of a quaternary salt of the following formula (II-a):

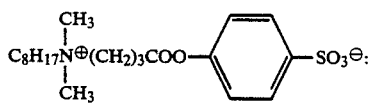

yield: 99.8%.

40.8 g of the compound (II-a) was dissolved in 4 l of a solvent mixture of ethanol/water (1:3) and hydrolysis was conducted at room temperature for 3 or 4 days while the pH was kept at 12 to 12.5 with KOH. After confirming that the starting quaternary salt had been spent according to TLC, the reaction mixture was neutralized with 20% sulfuric acid and the solvent was distilled off while a salt formed was filtered off. A remaining oily substance was desalted with dichloromethane to obtain 28.0 g of an amphoteric surfactant of the following formula (III-a):

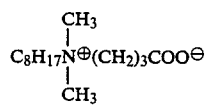

yield: 99.4%.

46.5 g of the compound (III-a) was dissolved in 250 ml of dichloromethane in a 500-ml two-necked flask. 20 ml of thionyl chloride was added dropwise to the solution at room temperature and the reaction was conducted under reflux for 1 h. The solvent and excess thionyl chloride were distilled off to obtain 57.0 g of a compound of the following formula (IV-a) as an orange oily substance:

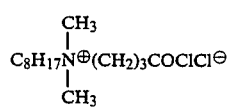

yield: 100%.

50.0 g of the acyl chloride (IV-a) was dissolved in 400 ml of dimethoxyethane (DME) which had been dehydrated with lithium aluminum hydride and distilled. Disodium p-phenolsulfonate prepared by a process which will be described hereinbelow was added to the solution and the suspension thus obtained was reacted under reflux for 2 h. DME was removed by decantation. Acetone was added thereto and the mixture was stirred at room temperature. An acetone-soluble matter was removed by filtration to obtain a mixture of sodium chloride with the compound (I-a). By recrystallization from ethanol/acetone, 26.8 g of white platy crystals were obtained.

yield: 40.0%.

m.p. 217°~227° C.

IR (KBr, cm$^{-1}$): 2932, 2860, 1758, 1491, 1197, 1152, 1122, 1029, 1011, 687, 567

$^1$H-NMR (CD$_3$OD solvent, TMS internal standard, δ): 1.0 (3H, t), 1.3~1.5 (12H, m), 2.1~2.2 (2H, m), 2.7 (2H, t), 3.05 (6H, s), 3.35~3.45 (2H, m), 7.2 (2H, d), 7.85 (2H, d)

Preparation of disodium p-phenolsulfonate 278.4 g of sodium p-phenolsulfonate dihydrate was dissolved in 200 ml of water. 52 g of sodium hydroxide was added to the solution and the mixture was stirred at room temperature for 2 h. Disodium p-phenolsulfonate thus crystallized out was separated by filtration. The filtrate was further subjected to the recrystallization. The crystals were dehydrated with a Dean-Stark reflux condenser using toluene as the solvent and then refluxed through a molecular sieve to thoroughly dehydrate them. 228 g of disodium p-phenolsulfonate was obtained.

yield: 87.4%.

Example 2

Preparation of

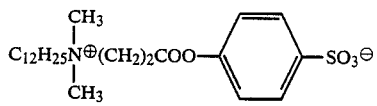
(I-b)

The compound (I-b) was prepared in the same manner as that of Example 1 except that dimethyloctylamine was replaced with dimethyldodecylamine.

The yield obtained after the 4-stage reaction was 53.8%.

m.p. 213°~216° C.

IR (KBr, cm$^{-1}$): 2920, 2854, 1755, 1497, 1470, 1221, 1191, 1122, 1032, 1011, 693, 567

$^1$H-NMR (CD$_3$OD, TMS internal standard, δ): 0.9 (3H, t), 1.2~1.45 (20H, m), 1.7~1.9 (2H, m), 2.05~2.2 (2H, m), 2.73 (2H, t), 3.09 (6H, s), 3.3~3.45 (2H, m), 7.15 (2H, d), 8.87 (2H, d)

Example 3

Preparation of

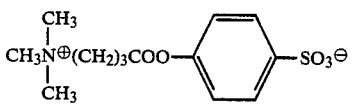
(I-c):

52 g of ethyl bromoacetate was dissolved in 250 ml of acetone in a 1,000-ml three-necked flask. Dry gaseous trimethylamine carried by N$_2$ gas was bubbled through the solution under stirring with a magnetic stirrer. After two equivalents of trimethylamine per equivalent of ethyl bromoacetate was bubbled over a period of 3 h, the flask was closed and the mixture was stirred at room temperature overnight. White crystals thus formed were separated by filtration to obtain 57.9 g of a compound of the following formula (II-c):

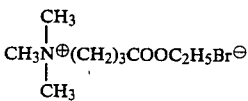
(II-c)

yield: 85.4%.

50.65 g of the compound (II-c) was dissolved in 1 l of a solvent mixture of ethanol/water (1:1) and hydrolysis was conducted at room temperature for 3 or 4 days while the pH was kept at 12 to 12.5 with KOH. After confirming that the starting quaternary salt had been spent according to TLC, the reaction mixture was neutralized with 20% sulfuric acid and the solvent was distilled off while a salt formed was filtered off. A remaining oily substance was desalted with methanol to obtain 32.7 g of an amphoteric compound of the following formula (III-c):

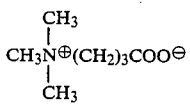
(III-c)

yield: 99.0%.

Thereafter, the same procedure as that of Example 1 was repeated to obtain the compound of the formula (I-c). The yield obtained after the 4-stage reaction was 42.5%.

IR (KBr, cm$^{-1}$): 3034, 1749, 1593, 1494, 1194, 1071, 1029, 1011, 699, 567

$^1$H-NMR (D$_2$O, DSS internal standard, δ): 0.9~2.5 (4H, m), 2.7 (2H, t), 3.1 (9H, t), 7.2 (2H, d), 7.9 (2H, d)

EXAMPLE 4

Synthesis of

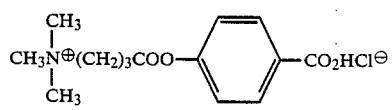
(I-d)

In a three-necked flask having a capacity of 1000 ml, 52 g of ethyl bromobutyrate was dissolved in 250 cc of acetone, and the solution was bubbled by dry trimethylamine by using gaseous N$_2$ as a carrier gas under stirring with a magnetic stirrer. Trimethylamine was passed through the solution in an amount of 2 equivalents to ethyl bromobutyrate over a period of 3 hours. Then, the flask was sealed and the reaction liquid was stirred at room temperature overnight.

The formed white crystal was recovered by filtration to obtain 57.9 g of (II-d) in a yield of 85.4%:

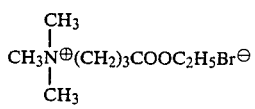
(II-d)

Then, 50.65 g of (II-d) was dissolved in 1 l of a mixed solvent of ethanol/water (1/1) and hydrolysis was conducted at room temperature for 3 to 4 days while maintaining the pH value at 12 to 12.5 with KOH. After consumption of the starting quaternary salt was confirmed by TLC, the reaction liquid was neutralized with 20% sulfuric acid, and the solvent was removed by distillation while performing the filtering operation when a salt was formed. The salt was removed from the remaining oily substance by using methanol to obtain 32.7 g of a substance of the following formula (III-d) in a yield of 99.0%:

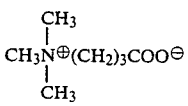
(III-d)

In a two-necked flask having a capacity of 2000 ml, 220.3 g of (III-d) was dissolved in 300 g of chloroform, and 361.6 g of thionyl chloride was dropped to the solution at room temperature. A reaction was carried out under reflux for 1 hour. Removal of the solvent and excessive thionyl chloride by distillation gave 369.4 g of (IV-d) in the form of an orange oily substance.

(the yield was 121.6%):

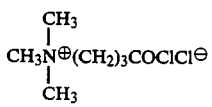
(IV-d)

In a three-necked flask having a capacity of 5000 ml, 209.7 g of p-hydroxybenzoic acid was dissolved in 2100 g of THF and 477.1 g of dimethyloctylamine was added to the solution. 369.4 g of the acid chloride obtained above was added dropwise to the solution at room temperature with stirring. After termination of the dropwise addition, the reaction liquid was stirred at room temperature for 1 hour and filtered, and the obtained crystal was washed with acetone and acetic acid to obtain 22.8 g of a crude hydrochloride of (I-d) in a yield of 48.2%:

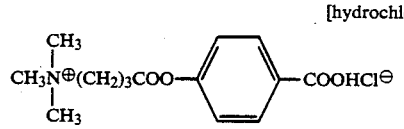
[hydrochloride of (I-d)]

Physical Properties of (I-d)
Melting point: 250° to 253° C.
IR (KBr, cm$^{-1}$): 3010, 2830, 2570, 1758, 1704, 1611, 1419, 1383, 1227, 1167, 1116, 1098, 909, 867
$^1$H-NMR (CD$_3$OD solvent, TMS internal standard δ): 1.95–2.5 (2H, m), 2.8 (2H, t), 3.2 (9H, s), 3.5 (2H, t), 7.25 (2H, d), 8.1 (2H, d)

EXAMPLE 5

Synthesis of

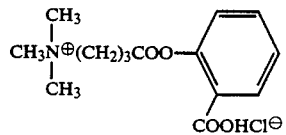
(I-e)

In a three-necked flask having a capacity of 5000 ml, 194.4 g of salicylic acid was dissolved in 1500 g of THF and 442.4 g of dimethyloctylamine was added to the solution. 339.1 g of the acid chloride (IV-d) obtained according to the process of Example 4 was added dropwise to the solution at room temperature. After termination of the dropwise addition, the reaction liquid was stirred at room temperature for 1 hour and filtered. The obtained crystal was washed with acetone to obtain 269.1 g of a hydrochloride of the formula (I-e) in a yield of 63.3%:

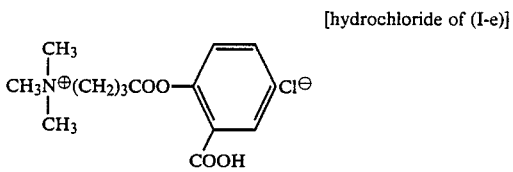
[hydrochloride of (I-e)]

Physical Properties of (I-e)
Melting point: 167° to 171° C.
IR (KBr, cm$^{-1}$): 3016, 2740, 2578, 1764, 1710, 1611, 1491, 1455, 1416, 1389, 1272, 1245, 1203, 1155, 1119, 1083, 792, 747
$^1$H-NMR (CD$_3$OD, TMS internal standard δ) 1.8–2.5 (2H, m), 2.75 (2H, t), 3.2 (9H, s) 3.5 (2H, t), 7.1–8.2 (4H, m)

EXAMPLE 6

The obtained compounds (I-a), (I-b), (I-d) and (I-e) were examined in the test on the bleaching action. Results of evaluation of the bleaching effect according to the method described below are shown in Table 1.

Bleaching Method

Hydrogen peroxide was added to 300 ml of water at 20° C. so that the effective oxygen concentration was 0.05% and 1 g of sodium carbonate was added. The compounds (I-a), (I-b), (I-d) and (I-e) were added to the respective solutions in an equimolar amount to hydrogen peroxide. A black tea-stained fabric prepared according to the method described below was immersed in the solution for 30 minutes. The fabric was washed with water and dried, and the bleaching ratio was calculated according to the formula described below. Sodium hypochlorite as a comparative sample was evaluated at an effective chlorine concentration of 0.06%.

Bleaching Ratio of Black Tea-stained Fabric:

$$\text{Bleaching ratio (\%)} = \frac{\text{reflectance after bleaching} - \text{reflectance before bleaching}}{\text{reflectance of white fabric} - \text{reflectance before bleaching}} \times 100$$

The reflectance was measured by using NDR-101DP supplied by Nippon Denshoku Kogyo K. K. and a 460 nm filter.

Black Tea-stained Fabric:

TABLE 1

|  |  | Present invention | | | | Comparative | |
|---|---|---|---|---|---|---|---|
|  |  | 1 | 2 | 3 | 4 | 5 | 6 |
| Component and its conc. in solution (%) | H$_2$O$_2$ | 0.106 | 0.106 | 0.106 | 0.106 | 0.106 | — |
|  | I-a | 1.25 | — | — | — | — | — |
|  | I-b | — | 1.42 | — | — | — | — |
|  | I-d | — | — | 1.02 | — | — | — |
|  | I-e | — | — | — | 1.02 | — | — |
|  | NaOCl | — | — | — | — | — | 0.063 |
|  | Na$_2$CO$_3$ | 0.333 | 0.333 | 0.333 | 0.333 | 0.333 | — |
|  | NaOH | — | — | — | — | — | 0.01 |
| Available oxygen concentration (%) |  | 0.05 | 0.05 | 0.05 | 0.05 | 0.05 | — |
| Available chlorine concentration (%) |  | — | — | — | — | — | 0.06 |

TABLE 1-continued

|  | Present invention | | | | Comparative | |
|---|---|---|---|---|---|---|
|  | 1 | 2 | 3 | 4 | 5 | 6 |
| Bleaching ratio (%) | 78 | 70 | 75 | 74 | 21 | 63 |

In 3 l of deionized water, 80 g of black tea (Yellow Package supplied by Nitto Kocha) was boiled for about 15 minutes, and the liquid was filtered through a paste-free bleached cotton cloth, and a cotton fabric of shirting #2003 was immersed in the liquid and boiled for about 15 minutes. The fabric was taken out, allowed to stand still for about 2 hours and spontaneously dried. Then, the fabric was washed with water until the washing became colorless. The fabric was dehydrated, pressed and cut into a size of 10 cm×10 cm, and the obtained test piece was subjected to the test.

EXAMPLE 7

A bleaching composition as shown in Table 2 was prepared from each activator obtained in Examples 1 and 2.

The bleaching effect of the composition was examined to obtain the results shown in Tables 2 and 3.

Bleaching Effects Obtained by Immersion Bleaching method (Table 2)

Sodium percarbonate was dissolved in 300 ml of water at 20° C. to obtain a solution having an available oxygen concentration of 0.05%. The activator was added to the solution in an amount equimolar to hydrogen peroxide. Five sheets (8 cm×8 cm) of a cloth stained with black tea prepared as will be described below were immersed therein for 30 min, washed with water and dried. The bleaching rate was determined according to the following equation. The available oxygen concentration of comparative magnesium monoperphthalate hexahydrate was 0.05% and available chlorine concentration of comparative sodium hypochlorite was 0.06%.

Bleaching rate of cloth stained with black tea:

Bleaching rate (%) =

$$\frac{\left(\begin{array}{c}\text{reflectivity}\\\text{after bleaching}\end{array}\right) - \left(\begin{array}{c}\text{reflectivity}\\\text{before bleaching}\end{array}\right)}{\left(\begin{array}{c}\text{reflectivity of}\\\text{white cloth}\end{array}\right) - \left(\begin{array}{c}\text{reflectivity}\\\text{before bleaching}\end{array}\right)} \times 100$$

The reflectivity was determined with NDR-101DP (a product of Nippon Denshoku Denko Co., Ltd.) using a 460 nm filter.

Cloth stained with black tea:

80 g of black tea leaves (yellow packages of Nitto Black Tea) were boiled in 3 l of ion-exchanged water for about 15 min and then filtered through a desized, bleached cotton cloth. A cotton shirting #2003 was immersed in the filtrate under boiling for about 15 min. The mixture was left to stand without heating for 2 h and then spontaneously dried. The cloth was washed with water until the wash water was no more colored, then dehydrated and pressed. The cloth was cut into test pieces having a size of 8 cm×8 cm, which were examined in the tests.

TABLE 2

| | | Present invention | | Comparative | | | |
|---|---|---|---|---|---|---|---|
| | | 7(3) | 8(3) | 9(3) | 10(3) | 11(4) | 12(3) |
| Component | Sodium percarbonate | 23 | 20 | 68 | — | — | 100 |
| | I-a | 77 | — | — | — | — | — |
| | I-b | — | 80 | — | — | — | — |
| | TAED(1) | — | — | 32 | — | — | — |
| | Magnesium mono-perphthalate(2) | — | — | — | 85 | — | — |
| | NaOCl | — | — | — | — | 6.3 | — |
| | Na2CO3 | — | — | — | 15 | — | — |
| | NaOH | — | — | — | — | 0.5 | — |
| | Water | — | — | — | — | balance | — |
| Bleaching rate (%) | | 78 | 70 | 51 | 58 | 63 | 21 |

(1)tetraacetylethylenediamine (a product of Hoechst)
(2)a product of INTEROX
(3)solution having an available oxygen concentration of 0.05%
(4)solution having an available chlorine concentration of 0.06%

Bleaching Effects of a Bleaching Composition Used in Combination With a Detergent (Table 3)

Five sheets (8 cm×8 cm) of the cloth stained with black tea prepared as described above were washed with a wash solution containing 0.133% of a commercially available heavy duty detergent and the detergent composition 7, 8, 9, 10 or 12 shown in Table 2 in such an amount that the available oxygen concentration would be 0.0033% with a turgotometer at 20° C. for 10 min. They were then washed with water and dried. The bleaching rates of them were determined by the above-mentioned method. In case of the comparative sample 11, the bleaching agent was added to the detergent of the above-mentioned concentration in such an amount that the available chlorine concentration would be 0.014% and the bleaching rate was determined in the same manner as that described above.

TABLE 3

| | Present invention | | Comparative | | | |
|---|---|---|---|---|---|---|
| Bleaching composition | 7(1) | 8(1) | 9(1) | 10(1) | 11(2) | 12(1) |
| Bleaching rate (%) | 41 | 27 | 10 | 11 | 38 | 3 |

(1)available oxygen concentration: 0.0033%
(2)available chlorine concentration: 0.014%

EXAMPLE 8

The three bleaching compositions, containing no phosphorus, a small amount of phosphorus and a considerable amount of phosphorus, respectively, were obtained in the below shown formulations. Percent is based on weight.

The composition containing no phosphorus was obtained from 14% of sodium linear dodecylbenzene sulfonate, 6% of polyoxyethylene (10 moles of EO) C12 to C13 alkyl ether, 2% of sodium salt of hardened beef tallow aliphatic acid, 5% of sodium silicate of 2 go, 10% of sodium carbonate, 25% of zeolite of the 4A type, 10% of sodium percarbonate, 10% of the amphoteric compound (I-a), 2% of polyethylene glycol having a molecular weight of 6,000, 2% of protease, 4% of water and the balance of sodium sulfate.

The compound having a small amount of phosphorus was obtained from 10% of sodium linear dodecylbenzene sulfonate, 2% of sodium dodecylsulfate, 8% of polyoxyethylene (7.7 moles of EO) C12 to C13 alkyl ether, 2% of sodium salt of hardened beef tallow aliphatic acid, 5% of sodium silicate of 1 go, 10% of sodium carbonate, 20% of zeolite of the 4A type, 15% of sodium pyrophosphate, 10% of sodium perborate, 5% of the amphoteric compound (I-e), 1% of polyethylene glycol having a molecular weight of 11,000, 1% of sodium sulfite, 2% of protease, 4% of water and the balance of sodium sulfate.

The compound containing a considerable amount of phosphorus was obtained from 20% of polyoxyethylene (8.6 moles of EO) beef tallow alcohol ether, 2% of sodium salt of hardened beef tallow aliphatic acid, 30% of sodium tripolyphosphate, 10% of sodium perborate, 5% of the amphoteric compound (I-c), 5% of sodium silicate of 2 go, 10% of sodium carbonate, 1% of sodium sulfite, 2% of polyethylene glycol having a molecular weight of 6,000, 2% of protease, 6% of water and the balance of sodium sulfate.

What is claimed is:

1. A bleaching composition, comprising:
a peroxide bleaching agent, and
an amphoteric organic per acid precursor or its salt having the formula

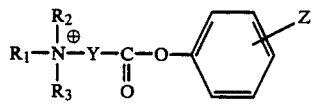

wherein $R_1$ and $R_2$ each represents a substituted or unsubstituted, straight chain or branched alkyl or alkenyl having 1 to 30 carbon atoms, alkaryl in which the alkyl has 1 to 24 carbon atoms, or

forms a heterocyclic ring having 4 to 6 carbon atoms; $R_3$ represents a substituted or unsubstituted, straight-chain or branched alkyl or alkenyl group having 1 to 30 carbon atoms, alkaryl in which the alkyl group has 1 to 16 carbon atoms, $-(C_2H_4O)_xH$ in which x is a number of from 1 to 20 or

forms a heterocyclic ring having 4 to 6 carbon atoms; Y represents a straight-chain or branch alkylene having 1 to 20 carbon atoms, and Z represents $SO_3^-$, $CO_2^-$, or a hydrohalide thereof.

2. A composition as claimed in claim 1 in which said peroxide bleaching agent is hydrogen peroxide or a peroxide effective to release hydrogen peroxide in an aqueous solution.

3. A bleaching detergent composition comprising a bleaching composition as claimed in claim 1 in combination with a water-soluble, synthetic, organic surface active material.

4. A composition as claimed in claim 1 in which the molar ratio of said peroxide bleaching agent/said amphoteric organic per acid precursor is from 99.9/0.1 to 20/80.

5. A composition as claimed in claim 1 in which said peroxide bleaching agent is selected from the group consisting of sodium carbonate/hydrogen peroxide adduct, sodium tripolyphosphate/hydrogen peroxide adduct, $4Na_2SO_4.2H_2O_2.NaCl$, sodium pyrophosphate/hydrogen peroxide adduct, urea/hydrogen peroxide adduct, sodium perborate monohydrate, sodium perborate tetrahydrate, sodium peroxide and calcium peroxide.

6. A composition as claimed in claim 1 in which said amphoteric organic acid precursor has the formula

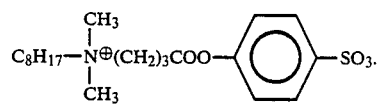

7. A composition as claimed in claim 1 in which said amphoteric organic acid precursor has the formula

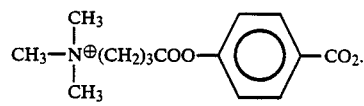

8. A bleaching composition, comprising:
a peroxide bleaching agent, and
an amphoteric organic per acid precursor having the formula

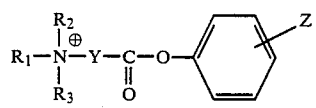

wherein $R_1$ is alkyl or hydroxyalkyl having 1 to 22 carbon atoms; $R_2$ and $R_3$ each represents alkyl having 1 to 3 carbon atoms; Y is alkylene having 1 to 5 carbon atoms; and Z represents $SO_3^-$, $CO_2^-$, or a hydrohalide thereof.

9. A composition as claimed in claim 8 in which said peroxide bleaching agent is hydrogen peroxide or a peroxide effective to release hydrogen peroxide in an aqueous solution.

10. A bleaching detergent composition comprising a bleaching composition as claimed in claim 8 in combination with a water-soluble, synthetic, organic surface active material.

11. A composition as claimed in claim 8 in which the molar ratio of said peroxide bleaching agent/said amphoteric organic per acid precursor is from 99.9/0.1 to 20/80.

12. A composition as claimed in claim 8 in which said peroxide bleaching agent is selected from the group consisting of sodium carbonate/hydrogen peroxide adduct, sodium tripolyphosphate/hydrogen peroxide adduct, $4Na_2SO_4.2H_2O_2.NaCl$, sodium pyrophosphate/hydrogen peroxide adduct, sodium perborate monohydrate, sodium perborate tetrahydrate, sodium peroxide and calcium peroxide.
13. A composition as claimed in claim 8 in which said amphoteric organic acid precursor has the formula
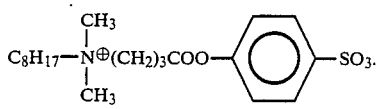
14. A composition as claimed in claim 8 in which said amphoteric organic acid precursor has the formula
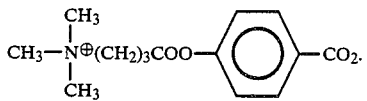
* * * * *